US006632605B1

(12) United States Patent
Cronin et al.

(10) Patent No.: US 6,632,605 B1
(45) Date of Patent: *Oct. 14, 2003

(54) HYBRIDIZATION ASSAYS ON OLIGONUCLEOTIDE ARRAYS (75) Inventors: Maureen T. Cronin, Los Altos, CA (US); Garry Miyada, San Jose, CA (US); Mark Trulson, San Jose, CA (US); Thomas R. Gingeras, Encinitas, CA (US); Glenn McGall, Mountain View, CA (US); Claire Robinson, Palo Alto, CA (US); Michelle Smedsrud-Oval, Coronado, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/393,389

(22) Filed: Sep. 10, 1999

Related U.S. Application Data (63) Continuation of application No. 08/648,709, filed on May 16, 1996, now Pat. No. 6,045,996, which is a continuation-in-part of application No. 08/544,381, filed on Oct. 10, 1995, now Pat. No. 6,027,880, which is a continuation-in-part of application No. 08/510,521, filed on Aug. 2, 1995, which is a continuation-in-part of application No. PCT/US94/12305, filed on Oct. 26, 1994, which is a continuation-in-part of application No. 08/284,064, filed on Aug. 2, 1994, now abandoned, which is a continuation-in-part of application No. 08/143,312, filed on Oct. 26, 1993, now abandoned.

(51) Int. Cl.[7] .......................... C12Q 1/68; G01N 15/00; C12M 1/00; G06F 19/00
(52) U.S. Cl. ....................... 435/6; 422/68.1; 435/287.1; 435/287.2; 702/20
(58) Field of Search .......................... 435/6, 4, 287.1, 435/287.2; 436/501; 422/68.1; 702/20

(56) References Cited

U.S. PATENT DOCUMENTS

| 4,483,920 | A | 11/1984 | Gillespie et al. ............... 435/6 |
| 4,652,517 | A | 3/1987 | Scholl et al. .................... 435/5 |
| 5,015,569 | A | 5/1991 | Pontius .......................... 435/6 |
| 5,143,854 | A | 9/1992 | Pirrung et al. ............... 436/518 |
| 5,324,633 | A | 6/1994 | Fodor et al. .................... 435/6 |
| 5,412,087 | A | 5/1995 | McGall et al. .............. 536/24.3 |
| 5,445,934 | A | 8/1995 | Fodor et al. .................... 435/6 |
| 5,521,061 | A | 5/1996 | Bresser et al. .................. 435/5 |
| 5,632,957 | A | 5/1997 | Heller et al. .................... 435/6 |
| 6,045,996 | A | * 4/2000 | Cronin et al. ................... 435/6 |

FOREIGN PATENT DOCUMENTS

| EP | 0 167 366 | 1/1986 |
| EP | 0 229 441 | 7/1987 |
| WO | WO 87/06621 | 11/1987 |
| WO | WO 90/15070 | 12/1990 |
| WO | WO 92/10092 | 6/1992 |
| WO | WO 92/10588 | 6/1992 |
| WO | WO 95/00530 | 1/1995 |
| WO | WO 95/11995 | 5/1995 |

OTHER PUBLICATIONS

Hames et al. (1985) *Nucleic Acid Hybridization, A Practical Approach* IRL Press Limited, Oxford, England. pp. 6, 64, 65, 79, 190–191. See entire disclosure.
Khrapko et al (1989). "An oligonucleotide hybridization approach to DNA sequencing," *FEBS Letters* 256: 118–122.
Melchior et al. (1983). "Alteration of the relative stability of dA–dT and dG–dC base pairs in DNA," *Proc. Natl. Acad. Sci. USA* 70 (20): 298–302.
Pease et al. (1994). "Light–generated oligonucleotide arrays for rapid DNA sequence analysis," *Proc. Natl. Acad. Sc., USA* 91:5022–5026.
Pontius (1993). "Close encounters: Why unstructured, polymeric domains can increase rates of specific macromolecular association," *TIBS* 18:181–186.

(List continued on next page.)

*Primary Examiner*—Ardin H. Marschel
(74) *Attorney, Agent, or Firm*—Schwegman, Lundberg, Woessner & Kluth, P.A.

(57) ABSTRACT

This invention provides methods of performing nucleic acid hybridization assays on high-density substrate-bound oligonucleotide arrays involving including in the hybridization mixture an isostabilizing agent, a denaturing agent or a renaturation accelerant.

22 Claims, 2 Drawing Sheets

OTHER PUBLICATIONS

Pontius et al. (1990) "Renaturation of complementary DNA strands mediated by purified mammalian heterogeneous nuclear ribonucleoprotein A1 protein: Implications for a mechanism for rapid molecular assembly," *Proc. Natl. Acad. Sci. USA* 87:8403–8407.

Pontius et al. (1991), "Rapid renaturation of complementary DNA strands mediated by cationic detergents: A role for high–probability binding domains in enhancing the kinetics of molecular assembly processes," *Proc. Natl. Acad. Sci. USA* 88:8237–8241.

Rees et al. (1993). "Betaine can eliminate the base pair composition dependence of DNA melting," *Biochemistry* 32:137–144 (1993).

Sambrook et al. (1989) "Hybridization of pools of oligonucleotides," *Molecular Cloning, A Laboratory manual, Second Edition, Cold Spring Harbor Laboratory press* pp. 11.48–11.51.

Van Ness et al. (1991) "The use of oligodeoxynucleotide probes in chaotropbased hybridization solutions," *Nucleic Acids Research* 19(19):5143–5151.

Wetmur (1991). "DNA Probes: Applications of the principles of Nucleic Acid Hybridization," *Critical Reviews in Biochemistry and Molecular Biology* 26(3/4):227–259.

Wood (1985). "Base composition–independent hybridization in tetramethylammonium chloride: A method for oligonucleotide screening of highly complete gene libraries," *Proc. Natl. Acad. Sci, USA*, 82:1585–1588.

Young et al. (1983). "Efficient isolation of genes by using antibody probes," *Proc. Natl. Acad. Sci. USA* 80:1194–1198.

* cited by examiner

FIG. 1

FIG. 2 ns. Modifications in custom array designs have contributed to simplifying this problem. However, certain modifications, such as length variation, are not an option in combinatorial arrays. Therefore, methods of normalizing the signal between hybrids of different sequences would be very useful in applications of high density substrate-bound oligonucleotide arrays that generate large amounts of data in hybridization assays.

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
       (A) LENGTH: 20 base pairs
       (B) TYPE: nucleic acid
       (C) STRANDEDNESS: single
       (D) TOPOLOGY: linear     (ii) MOLECULE TYPE: DNA     (xi) SEQUENCE DESCRIPTION: SEQ ID NO: 1:

CTGAACGGTA GCATCTTGAC                                       20

(2) INFORMATION FOR SEQ ID NO: 2:

(i) SEQUENCE CHARACTERISTICS:
       (A) LENGTH: 27 base pairs
       (B) TYPE: nucleic acid
       (C) STRANDEDNESS: single
       (D) TOPOLOGY: linear     (ii) MOLECULE TYPE: DNA     (xi) SEQUENCE DESCRIPTION: SEQ ID NO: 2:

GCAGAGATGG AGAAGGTGAG AGTGGCT                               27

(2) INFORMATION FOR SEQ ID NO: 3:

(i) SEQUENCE CHARACTERISTICS:
       (A) LENGTH: 25 base pairs
       (B) TYPE: nucleic acid
       (C) STRANDEDNESS: single
       (D) TOPOLOGY: linear     (ii) MOLECULE TYPE: DNA     (xi) SEQUENCE DESCRIPTION: SEQ ID NO: 3:

CATAGTGGTG GCTGACCTGT TCTCT                                 25

(2) INFORMATION FOR SEQ ID NO: 4:

```
    (i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

CATAGTGGTG GGTAACCTGT TCCTT                                              25
```

HYBRIDIZATION ASSAYS ON OLIGONUCLEOTIDE ARRAYS

CROSS-REFERENCE TO RELATED APPLICATIONS

This application is a continuation of U.S. application Ser. No. 08/648,709, filed May 16, 1996, now U.S. Pat. No. 6,045,996, which is a continuation-in-part of U.S. application Ser. No. 08/544,381, filed Oct. 10, 1995, now U.S. Pat. No. 6,027,880, which is a continuation-in-part of pending U.S. application Ser. No. 08/510,521, filed Aug. 2, 1995, which is a continuation-in-part of pending International application PCT/US94/12305, filed Oct. 26, 1994, which is a continuation-in-part of U.S. application Ser. No. 08/284,064, filed Aug. 2, 1994, now abandoned, which is a continuation-in-part of U.S. application Ser. No. 08/143,312, filed Oct. 26, 1993, now abandoned, all of which are incorporated herein in their entirety.

BACKGROUND OF THE INVENTION

This invention relates to methods for improving the discrimination of hybridization of target nucleic acids to probes on substrate-bound oligonucleotide arrays. Therefore, it relates to the fields of molecular biology and biophysics.

Substrate-bound oligonucleotide arrays, such as the Affymetrix DNA Chip, enable one to test hybridization of a target nucleic acid molecule to many thousands of differently sequenced oligonucleotide probes at feature densities greater than a five hundred per 1 $cm^2$. Because hybridization between two nucleic acids is a function of their sequences, analysis of the pattern of hybridization provides information about the sequence of the target molecule. The technology is useful for de novo sequencing and re-sequencing of nucleic acid molecules. The technology also has important diagnostic uses in discriminating genetic variants that may differ in sequence by one or a few nucleotides. For example, substrate-bound oligonucleotide arrays are useful for identifying genetic variants of infectious diseases, such as HIV, or genetic diseases, such as cystic fibrosis.

In one version of the substrate-bound oligonucleotide array, the target nucleic acid is labeled with a detectable marker, such as a fluorescent molecule. Hybridization between a target and a probe is determined by detecting the fluorescent signal at the various locations on the substrate. The amount of signal is a function of the thermal stability of the hybrids. The thermal stability is, in turn, a function of the sequences of the target-probe pair: AT-rich regions of DNA melt at lower temperatures than GC-rich regions of DNA. This differential in thermal stabilities is the primary determinant of the breadth of DNA melting transitions, even for oligonucleotides.

Depending upon the length of the oligonucleotide probes, the number of different probes on a substrate, the length of the target nucleic acid, and the degree of hybridization between sequences containing mismatches, among other things, a hybridization assay carried out on a substrate-bound oligonucleotide array can generate thousands of data points of different signal strengths that reflect the sequences of the probes to which the target nucleic acid hybridized. This information can require a computer for efficient analysis. The fact of differential fluorescent signal due to differences in thermal stability of hybrids complicates the analysis of hybridization results, especially from combinatorial oligonucleotide arrays for de novo sequencing and custom oligonucleotide arrays for specific re-sequencing applica-

SUMMARY OF THE INVENTION

The addition of hybridization optimizing agents, such as denaturing agents, isostabilizing agents or renaturation accelerants, to hybridization and/or wash buffers greatly improves signal resolution in hybridization assays performed on substrate-bound oligonucleotide arrays. This improvement is manifested as fewer total signals from the substrate due to decreases in the number of hybrids between mis-matched sequences, and normalization of signal strength among detectable hybrids.

Accordingly, this invention provides methods of performing hybridization assays between a target nucleic acid molecule and an oligonucleotide array having a surface to which are covalently attached oligonucleotide probes with different, known sequences, at discrete, known locations, the array having a density of at least 500 different features per square cm. The method involves incubating the array with a hybridization mixture comprising the target and a hybridization optimizing agent to allow hybridization and determining the identity of probes to which the target has hybridized. Preferably, the agent is an isostabilizing agent. Preferred isostabilizing agent is betaine. In one embodiment, the agent is not an alkyl ammonium ion. The arrays generally are high density arrays having at least five hundred, one thousand, ten thousand, one hundred thousand, or one million different features per square centimeter.

DETAILED DESCRIPTION OF THE INVENTION

I. DEFINITIONS

The following terms are intended to have the following general meanings as they are used herein:

A. Complementary: Refers to the topological compatibility or matching together of interacting surfaces of a probe molecule and its target. Thus, the target and its probe can be described as complementary, and furthermore, the contact surface characteristics are complementary to each other.

B. Probe: A probe is a surface-immobilized oligonucleotide that can be recognized by a particular target. Depending on context, the term "probe" refers both to individual oligonucleotide molecules and to the collection of same-sequence oligonucleotide molecules surface-immobilized at a discrete location.

C. Target: A nucleic acid molecule that has an affinity for a given probe. Targets may be naturally-occurring or man-made nucleic acid molecules. Also, they can be employed in their unaltered state or as aggregates with other species. Targets may be attached, covalently or noncovalently, to a binding member, either directly or via a specific binding substance. Targets are sometimes referred to in the art as anti-probes. A "Probe-Target Pair" is formed when two macromolecules have combined through molecular recognition to form a complex.

D. Feature: An area of a substrate having a collection of same-sequence, surface-immobilized oligonucleotide molecules. One feature is different than another feature if the probes of the different features have different nucleotide sequences.

E. Oligonucleotide Array: A substrate having a surface having at least two different features. oligonucleotide arrays preferably have a density of at least five hundred, at least one thousand, at least 10 thousand, at least 100 thousand, at least one million or at least 10 million features per square cm. In one embodiment, the arrays have a density of about 625 features per square cm. The substrate can be, merely by way of example, silicon or glass and can have the thickness of a glass microscope slide or a glass cover slip. Substrates that are transparent to light are useful when the method of performing an assay on the chip involves optical detection. As used herein, the term also refers to a probe array and the substrate to which it is attached that form part of a wafer.

II. Description

A. Performing Hybridization Assays

Hybridization assays on substrate-bound oligonucleotide arrays involve a hybridization step and a detection step. In the hybridization step, a hybridization mixture containing the target and an isostabilizing agent, denaturing agent or renaturation accelerant is brought into contact with the probes of the array and incubated at a temperature and for a time appropriate to allow hybridization between the target and any complementary probes. Usually, unbound target molecules are then removed from the array by washing with a wash mixture that does not contain the target, such as hybridization buffer. This leaves only bound target molecules. In the detection step, the probes to which the target has hybridized are identified. Since the nucleotide sequence of the probes at each feature is known, identifying the locations at which target has bound provides information about the particular sequences of these probes.

The hybridization mixture includes the target nucleic acid molecule and a hybridization optimizing agent in an appropriate solution, i.e., a hybridization buffer. The target nucleic acid molecule is present in the mixture at a concentration between about 0.005 nM target per ml hybridization mixture and about 50 nM target per ml hybridization mixture, preferably between about 0.5 nM/ml and 5 nM/ml or, more preferably, about 1 nM/ml and 2 nM/ml. The target nucleic acid molecule preferably includes a detectable label, such as a fluorescent label.

Including a hybridization "optimizing agent" in the hybridization mixture significantly improves signal discrimination between perfectly matched targets and single-base mismatches. As used herein, the term "hybridization optimizing agent" refers to a composition that decreases hybridization between mismatched nucleic acid molecules, i.e., nucleic acid molecules whose sequences are not exactly complementary.

As used herein, the term "isostabilizing agent" refers to a composition that reduces the base-pair composition dependence of DNA thermal melting transitions. More particularly, the term refers to compounds that, in proper concentration, result in a differential melting temperature of no more than about 1° C. for double stranded DNA oligonucleotides composed of AT or GC, respectively. Isostabilizing agents preferably are used at a concentration between 1 M and 10 M, between 2 M and 6 M, between 4 M and 6 M, between 4 M and 10 M and, optimally, at about 5 M. For example, 5 M agent in 2×SSPE is suitable. Betaines and lower tetraalkyl ammonium salts are examples of isostabilizing agents. In one embodiment, the isostabilizing agent is not an alkylammonium ion.

Betaine (N,N,N,-trimethylglycine; $(CH_3)_3N^+CH_2COO^-$) is the preferred isostabilizing agent. Rees et al. (Biochem. (1993) 32:137–144) have reported that betaine can eliminate the base pair composition dependence of DNA thermal stability. Unlike TMACl, betaine is zwitterionic at neutral pH and does not alter the polyelectrolyte behavior of nucleic acids while it does alter the composition-dependent stability of nucleic acids. Inclusion of betaine at about 5 M lowers the average hybridization signal about four fold, but increases the discrimination between matched and mismatched probes.

As used herein, a "lower tetraalkyl ammonium salt" is a tetramethyl or tetraethyl ammonium salt. Preferred are lower tetramethyl ammonium salts of the von Hippel series, e.g., those in which the counter ion is a halide (especially chloride), a phosphate or a sulfate. In particular, the lower tetraalkyl ammonium salt can be tetramethyl ammonium chloride ("TMACl") or tetraethyl ammonium chloride. (See, e.g., Melchior and von Hipple, *Proc. Natl. Acad. Sci. USA*, (1973) 70:298–302.) TMACl at a concentration of about 2.3 M is preferred.

As used herein, the term "denaturing agent" refers to compositions that lower the melting temperature of double stranded nucleic acid molecules by interfering with hydrogen bonding between bases in a double-stranded nucleic acid or the hydration of nucleic acid molecules. Denaturing agents can be included in hybridization buffers at concentrations of about 1 M to about 6 M and, preferably, about 3 M to about 5.5 M.

Denaturing agents include formamide, formaldehyde, DMSO ("dimethylsulfoxide"), tetraethyl acetate, urea, GuSCN, glycerol and chaotropic salts. As used herein, the term "chaotropic salt" refers to salts that function to disrupt van der Waal's attractions between atoms in nucleic acid molecules. Chaotropic salts include, for example, sodium trifluoroacetate, sodium tricholoroacetate, sodium perchlorate, guanidine thiocyanate ("GuSCN"), and potassium thiocyanate. GuSCN preferably is used at 2 M, and can be used at concentrations up to at least about 5 M.

As used herein the term "renaturation accelerant" refers to compounds that increase the speed of renaturation of nucleic acids by at least 100-fold. They generally have relatively unstructured polymeric domains that weakly associate with nucleic acid molecules. Accelerants include heterogenous nuclear ribonucleoprotein ("hnRP") Al and cationic detergents such as, preferably, CTAB ("cetyltrimethylammonium bromide") and DTAB ("dodecyl trimethylammonium bromide"), and, also, polylysine, spermine, spermidine, single stranded binding protein ("SSB"), phage T4 gene 32 protein and a mixture of ammonium acetate and ethanol. While not wishing to be limited by theory, renaturation accelerants appear to speed up renaturation by creating multi-step association reactions with reduced rates of dissociation of a highly dynamic encounter complex and provide an orientation-independent free energy of association, and create a new transition state that is less changed in translation and rotational entropy with respect to the reactants. B. W. Pontius, "*Close encounters: why unstructured, polymeric domains can increase rates of specific macromolecular association*," TIBS May 1993 pp 181–186. Renaturation accelerants can be included in hybridization mixtures at concentrations of about 1 μM to about 10 mM and, preferably, 1 μM to about 1 mM. The CTAB buffers work well at concentrations as low as 0.1 mM.

A variety of hybridization buffers are useful for the hybridization assays of the invention. By way of example, but not limitation, the buffers can be any of the following:

(1) 5 M Betaine, 1 M NaCl, pH 7.5
(2) 4.5 M Betaine, 0.5 M LiCl, pH 8.0
(3) 3 M TMACl, 50 mM Tris-HCl, 1 mM EDTA, 0.1% N-Lauroyl-Sarkosine (NLS)
(4) 2.4 M TEACl, 50 mM Tris-HCl, pH 8.0, 0.1% NLS
(5) 1 M LiCl, 10 mM Tris-HCl, pH 8.0, 10% Formamide
(6) 2 M GuSCN, 30 mM NaCitrate, pH 7.5
(7) 1 M LiCl, 10 mM Tris-HCl, pH 8.0, 1 mM CTAB
(8) 0.3 mM Spermine, 10 mM Tris-HCl, pH 7.5
(9) 2 M $NH_4OAc$ with 2 volumes absolute ethanol.

Addition of small amounts of ionic detergents (such as N-lauroyl-sarkosine) are useful. LiCl is preferred to NaCl. Hybridization can be at 20°–65° C., usually 37° C. to 45° C. for probes of about 14 nucleotides.

Additional examples of hybridization conditions are provided in several sources, including: Sambrook et al., *Molecular Cloning: A Laboratory Manual* (1989), 2nd Ed., Cold Spring Harbor, N.Y.; and Berger and Kimmel, "Guide to Molecular Cloning Techniques," *Methods in Enzymology*, (1987), Volume 152, Academic Press, Inc., San Diego, Calif.; Young and Davis (1983) *Proc. Natl. Acad. Sci.* (U.S.A.) 80: 1194.

The hybridization mixture is placed in contact with the array and incubated. Contact can take place in any suitable container, for example, a dish or a cell specially designed to hold the array and to allow introduction of the fluid into and removal of it from the cell so as to contact the array. Generally, incubation will be at temperatures normally used for hybridization of nucleic acids, for example, between about 20° C. and about 75° C., e.g., about 25° C., about 30° C., about 35° C., about 40° C., about 45° C., about 50° C., about 55° C., about 60° C. or about 65° C. For probes longer than about 14 nucleotides, 37° C.–45° C. is preferred. For shorter probes, 55° C.–65° C. is preferred. The target is incubated with the probe array for a time sufficient to allow the desired level of hybridization between the target and any complementary probes in the array. Using a hybridization temperature of 25° C. yields a very clear signal, usually in at least 30 minutes to two hours, but it may be desirable to hybridize longer, i.e., about 15 hours.

After incubation with the hybridization mixture, the array usually is washed with the hybridization buffer, which also can include the hybridization optimizing agent. These agents can be included in the same range of amounts as for the hybridization step, or they can be eliminated altogether. Then the array can be examined to identify the probes to which the target has hybridized.

B. Preparation of Target Samples

The target polynucleotide whose sequence is to be determined is usually isolated from a tissue sample. If the target is genomic, the sample may be from any tissue (except exclusively red blood cells). For example, whole blood, peripheral blood lymphocytes or PBMC, skin, hair or semen are convenient sources of clinical samples. These sources are also suitable if the target is RNA. Blood and other body fluids are also a convenient source for isolating viral nucleic acids. If the target is mRNA, the sample is obtained from a tissue in which the mRNA is expressed. If the polynucleotide in the sample is RNA, it is usually reverse transcribed to DNA. DNA samples or cDNA resulting from reverse transcription are usually amplified, e.g., by PCR. Depending on the selection of primers and amplifying enzyme(s), the amplification product can be RNA or DNA. Paired primers are selected to flank the borders of a target polynucleotide of interest. More than one target can be simultaneously amplified by multiplex PCR in which multiple paired primers are employed.

The target can be labelled at one or more nucleotides during or after amplification. For some target polynucleotides (depending on size of sample), e.g., episomal DNA, sufficient DNA is present in the tissue sample to dispense with the amplification step. Preferably, the detectable label is a luminescent label. Useful luminescent labels include fluorescent labels, chemi-luminescent labels, bioluminescent labels, and calorimetric labels, among others. Most preferably, the label is a fluorescent label such as a fluorescein, a rhodamine, a polymethine dye derivative, a phosphor, and so forth. Commercially available fluorescent labels include, inter alia, fluorescein phosphoramidites such as Fluoreprime (Pharmacia, Piscataway, N.J.), Fluoredite (Millipore, Bedford, Mass.) and FAM (ABI, Foster City, Calif.).

Useful light scattering labels include large colloids, and especially the metal colloids such as those from gold, selenium and titanium oxide.

Radioactive labels include, for example, $^{32}P$. This label can be detected by a phosphoimager. Detection, of course, depends on the resolution of the imager. Phosophoimagers are available having resolution of 50 microns. Accordingly, this label is currently useful with chips having features of at least that size.

When the target strand is prepared in single-stranded form as in preparation of target RNA, the sense of the strand should of course be complementary to that of the probes on the chip. This is achieved by appropriate selection of primers.

The target is preferably fragmented before application to the chip to reduce or eliminate the formation of secondary structures in the target. The average size of targets segments following hybridization is usually larger than the size of probe on the chip.

C. Substrate-bound OliQonucleotide Arrays Substrate-bound oligonucleotide arrays used in the assays of this invention typically include between about $5 \times 10^2$ and about $10^8$ features per square centimeter, or between about $10^4$ and about $10^7$, or between about $10^5$ and $10^6$.

Preferably, the arrays are produced through spatially directed oligonucleotide synthesis. As used herein, "spatially directed oligonucleotide synthesis" refers to any method of directing the synthesis of an oligonucleotide to a specific location on a substrate. Methods for spatially directed oligonucleotide synthesis include, without limitation, light-directed oligonucleotide synthesis, microlithography, application by ink jet, microchannel deposition to specific locations and sequestration with physical barriers. In general these methods involve generating active sites, usually by removing protective groups; and coupling to the active site a nucleotide which, itself, optionally has a protected active site if further nucleotide coupling is desired.

In one embodiment substrate-bound oligonucleotide arrays are synthesized at specific locations by light-directed oligonucleotide synthesis. The pioneering techniques of this method are disclosed in U.S. Pat. No. 5,143,854; PCT WO 92/10092; PCT WO 90/15070; and U.S. application Ser. Nos. 08/249,188, filed May 24, 1994, 07/624,120, filed Dec.

6, 1990, and 08/082,937, filed Jun. 25, 1993. In a basic strategy of this process, the surface of a solid support modified with linkers and photolabile protecting groups is illuminated through a photolithographic mask, yielding reactive hydroxyl groups in the illuminated regions. A 3'-O-phosphoranidite-activated deoxynucleoside (protected at the 5'-hydroxyl with a photolabile group) is then presented to the surface and coupling occurs at sites that were exposed to light. Following the optional capping of unreacted active sites and oxidation, the substrate is rinsed and the surface is illuminated through a second mask, to expose additional hydroxyl groups for coupling to the linker. A second 5'-protected, 3'-O-phosphoramidite-activated deoxynucleoside (C-X) is presented to the surface. The selective photodeprotection and coupling cycles are repeated until the desired set of products is obtained. Photolabile groups are then optionally removed and the sequence is, thereafter, optionally capped. Side chain protective groups, if present, are also removed. Since photolithography is used, the process can be miniaturized to generate high-density arrays of oligonucleotide probes.

This general process can be modified. For example, the nucleotides can be natural nucleotides, chemically modified nucleotides or nucleotide analogs, as long as they have activated hydroxyl groups compatible with the linking chemistry. The protective groups can, themselves, be photolabile. Alternatively, the protective groups can be labile under certain chemical conditions, e.g., acid. In this example, the surface of the solid support can contain a composition that generates acids upon exposure to light. Thus, exposure of a region of the substrate to light generates acids in that region that remove the protective groups in the exposed region. Also, the synthesis method can use 3'-protected 5'-O-phosphoramidite-activated deoxynucleoside. In this case, the oligonucleotide is synthesized in the 5' to 3' direction, which results in a free 5' end.

The general process of removing protective groups by exposure to light, coupling nucleotides (optionally competent for further coupling) to the exposed active sites, and optionally capping unreacted sites is referred to herein as "light-directed nucleotide coupling."

Tiling strategies for creating probe arrays adapted for various tasks, such as de novo sequencing or re-sequencing are described in U.S. patent application Ser. No. 08/510,521, filed Aug. 2, 1995 and International application PCT/US94/12305, filed Oct. 26, 1994.

If desired, the substrate-bound oligonucleotide array can be appropriately packaged for use in a chip reader. One such apparatus is disclosed in U.S. patent application Ser. No. 08/255,682, filed Jun. 8, 1994.

D. Detecting Fluorescently Labelled Probes

Determining a signal generated from a detectable label on an array requires an oligonucleotide array or chip reader. The nature of the oligonucleotide array reader depends upon the particular type of label attached to the target molecules.

In one embodiment the chip reader comprises a body for immobilizing the oligonucleotide array. Excitation radiation, from an excitation source having a first wavelength, passes through excitation optics from below the array. The excitation optics cause the excitation radiation to excite a region of an oligonucleotide array on the substrate. In response, labeled material on the sample emits radiation which has a wavelength that is different from the excitation wavelength. Collection optics, also below the array, then collect the emission from the sample and image it onto a detector. The detector generates a signal proportional to the amount of radiation sensed thereon. The signals can be assembled to represent an image associated with the plurality of regions from which the emission originated.

According to one embodiment, a multi-axis translation stage moves the oligonucleotide array in order to position different areas to be scanned, and to allow different locations of an array to be interrogated. As a result, a 2-dimensional image of the oligonucleotide array is obtained.

The oligonucleotide array reader can include an auto-focusing feature to maintain the sample in the focal plane of the excitation light throughout the scanning process. Further, a temperature controller may be employed to maintain the sample at a specific temperature while it is being scanned. The multi-axis translation stage, temperature controller, auto-focusing feature, and electronics associated with imaging and data collection are managed by an appropriately programmed digital computer.

In one embodiment, a beam is focused onto a spot of about 2 $\mu$m in diameter on the surface of the array using, for example, the objective lens of a microscope or other optical means to control beam diameter. (See, e.g., U.S. patent application Ser. No. 08/195,889, filed Feb. 10, 1994).

In another embodiment, fluorescent probes are employed in combination with CCD imaging systems. Details of this method are described in U.S. application Ser. No. 08/301,051, filed Sep. 2, 1994. In many commercially available microplate readers, typically the light source is placed above an array, and a photodiode detector is below the array. For the present methods, the light source can be replaced with a higher power lamp or laser. In one embodiment, the standard absorption geometry is used, but the photodiode detector is replaced with a CCD camera and imaging optics to allow rapid imaging of the array. A series of Raman holographic or notch filters can be used in the optical path to eliminate the excitation light while allowing the emission to pass to the detector. In a variation of this method, a fiber optic imaging bundle is utilized to bring the light to the CCD detector. In another embodiment, the laser is placed below the oligonucleotide array and light directed through the transparent wafer or base that forms the bottom of the oligonucleotide array. In another embodiment, the CCD array is built into the wafer of the oligonucleotide array.

The choice of the CCD array will depend on the number of oligonucleotides in each array. If 2500 features of sequence-specific oligonucleotides nominally arranged in a square (50×50) are examined, and 6 lines in each feature are sampled to obtain a good image, then a CCD array of 300×300 pixels is desirable in this area. However, if an individual array has 48,400 features (220×220) then a CCD array with 1320×1320 pixels is desirable. CCD detectors are commercially available from, e.g., Princeton Instruments, which can meet either of these requirements.

The detection device also can include a line scanner, as described in U.S. patent application Ser. No. 08/301,051, filed Sep. 2, 1994. Excitation optics focuses excitation light to a line at a sample, simultaneously scanning or imaging a strip of the sample. Surface-bound fluorescent labels from the array fluoresce in response to the light. Collection optics image the emission onto a linear array of light detectors. By employing confocal techniques, substantially only emission from the light's focal plane is imaged. Once a strip has been scanned, the data representing the 1-dimensional image are stored in the memory of a computer. According to one embodiment, a multi-axis translation stage moves the device at a constant velocity to continuously integrate and process data. Alternatively, galvometric scanners or rotating polyhedral mirrors may be employed to scan the excitation light across the sample. As a result, a 2-dimensional image of the sample is obtained.

In another embodiment, collection optics direct the emission to a spectrograph which images an emission spectrum onto a 2-dimensional array of light detectors. By using a spectrograph, a full spectrally resolved image of the array is obtained.

The read time for an oligonucleotide array will depend on the photophysics of the fluorophore (i.e., fluorescence quantum yield and photodestruction yield) as well as the sensitivity of the detector. For fluorescein, sufficient signal-to-noise to read a chip image with a CCD detector can be obtained in about 30 seconds using 3 mW/cm$^2$ and 488 nm excitation from an Arion laser or lamp. By increasing the laser power, and switching to dyes such as CY3 or CY5 which have lower photodestruction yields and whose emission more closely matches the sensitivity maximum of the CCD detector, one easily is able to read each array in less than 5 seconds.

A computer can transform the data into another format for presentation. Data analysis can include the steps of determining, e.g., fluorescent intensity as a function of substrate position from the data collected, removing "outliers" (data deviating from a predetermined statistical distribution), and calculating the relative binding affinity of the targets from the remaining data. The resulting data can be displayed as an image with color in each region varying according to the light emission or binding affinity between targets and probes therein.

One application of this system when coupled with the CCD imaging system that speeds performance when the detection step involves hybridization of a labeled target oligonucleotide with an oligonucleotide in the array is to obtain results of the assay by examining the on- or off-rates of the hybridization. In one version of this method, the amount of binding at each address is determined at several time points after the targets are contacted with the array. The amount of total hybridization can be determined as a function of the kinetics of binding based on the amount of binding at each time point. Thus, it is not necessary to wait for equilibrium to be reached. The dependence of the hybridization rate for different oligonucleotides on temperature, sample agitation, washing conditions (e.g., pH, solvent characteristics, temperature) can easily be determined in order to maximize the conditions for rate and signal-to-noise. Alternative methods are described in Fodor et al., U.S. Pat. No. 5,324,633, incorporated herein by reference.

The dependence of the hybridization rate for different oligonucleotides on temperature, sample agitation, washing conditions (e.g., pH, solvent characteristics, temperature) can easily be determined in order to maximize the conditions for rate and signal-to-noise.

E. Mechanics of Assays

Assays on oligonucleotide arrays generally include contacting an oligonucleotide array with a sample under the selected reaction conditions, optionally washing the array to remove unreacted molecules, and analyzing the biological array for evidence of reaction between target molecules the probes. These steps involve handling fluids. These steps can be automated using automated fluid handling systems for concurrently performing the detection steps on the array. Fluid handling allows uniform treatment of samples in the wells. Microtiter robotic and fluid-handling devices are available commercially, for example, from Tecan AG.

The chip can be manipulated by a fluid-handling device. This robotic device can be programmed to set appropriate reaction conditions, such as temperature, add reagents to the chip, incubate the chip for an appropriate time, remove unreacted material, wash the chip substrate, add reaction substrates as appropriate and perform detection assays. The particulars of the reaction conditions are chosen depends upon the purpose of the assay, for example hybridization of a probe or attachment of a label to oligonucleotides.

If desired, the chip can be appropriately packaged for use in chip reader. One such apparatus is disclosed in U.S. patent application Ser. No. 08/255,682, filed Jun. 8, 1994.

F. Substrate-bound Oligonucleotide Array Manufacture

In making a chip, the substrate and its surface preferably form a rigid support on which the sample can be formed. The substrate and its surface are also chosen to provide appropriate light-absorbing characteristics. For instance, the substrate may be functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, or combinations thereof. Other substrate materials will be readily apparent to those skilled in the art upon review of this disclosure. In a preferred embodiment the substrate is flat glass or silica.

Surfaces on the solid substrate usually, though not always, are composed of the same material as the substrate. Thus, the surface may be composed of any of a wide variety of materials, for example, polymers, plastics, resins, polysaccharides, silica or silica-based materials, carbon, metals, inorganic glasses, membranes, or any of the above-listed substrate materials. In one embodiment, the surface will be optically transparent and will have surface Si—OH functionalities, such as those found on silica surfaces.

Preferably, oligonucleotides are arrayed on a chip in addressable rows and columns. Technologies already have been developed to read information from such arrays. The amount of information that can be stored on each chip depends on the lithographic density which is used to synthesize the wafer. For example, if each feature size is about 100 microns on a side, each chip can have about 10,000 probe addresses (features) in a 1 cm$^2$ area.

The following examples are offered by way of illustration, not by way of limitation.

EXAMPLE

A 5.8 M solution of betaine was made in water (pH approx 5) and neutralized with NaOH. 9 ml of this solution was mixed with 1 ml 20×SSPE for a final solution concentration of 5.2 M betaine and 300 mM NaCl. Two chip arrays on a single wafer were used. These chips are designed to test for polymorphic differences in a cytochrome p450 gene, CYP-2D6. They include the complete coding sequence of the gene twice, exon by exon. They also include polymorphism tilings to detect specifically known polymorphisms. The top chip was hybridized with mixing in a tissue culture dish in 5×SSPE+1 mM CTAB and 1 nM of each of 4 oligonucleotide targets as follows:

Oligo 213 (control)5' CTGAACGGTA GCATCTTGA C 3'(SEQ ID NO:1)

Oligo ΔL281 5' GCAGAGATGG AGaagGTGAG AGTG-GCT 3'(SEQ ID NO:2)

E6P-CYP2D6 5' CATAGTGGTG G<u>CTG</u>ACCTGT TCTCT 3'(SEQ ID NO:3)

E6P-CYP2D7 5' CATAGTGGTG G<u>GTA</u>ACCTGT TCCTT 3'(SEQ ID NO:4)

The bottom chip was hybridized with 1 nM of the same four oligonucleotides in 1 ml of the betaine-NaCl solution mixing in a tissue culture dish. The hybridizations were for 30 minutes at room temperature.

Figure 1:
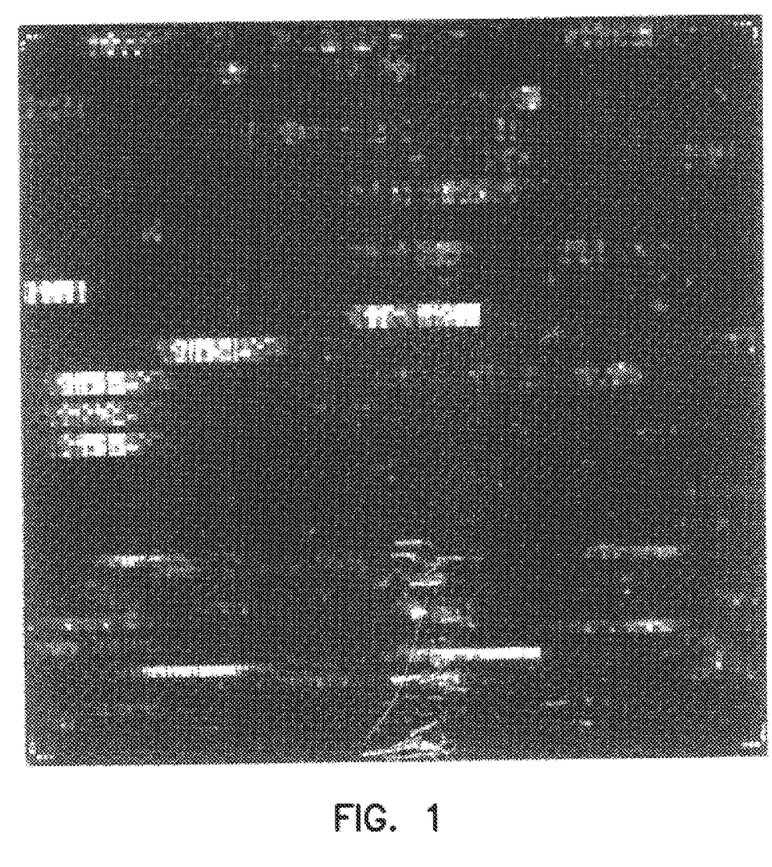
FIG. 1 is a scan of a substrate-bound oligonucleotide array hybridized with four oligonucleotide targets (SEQ ID NOS: 1–4) with 5×SSPE.
Figure 2:
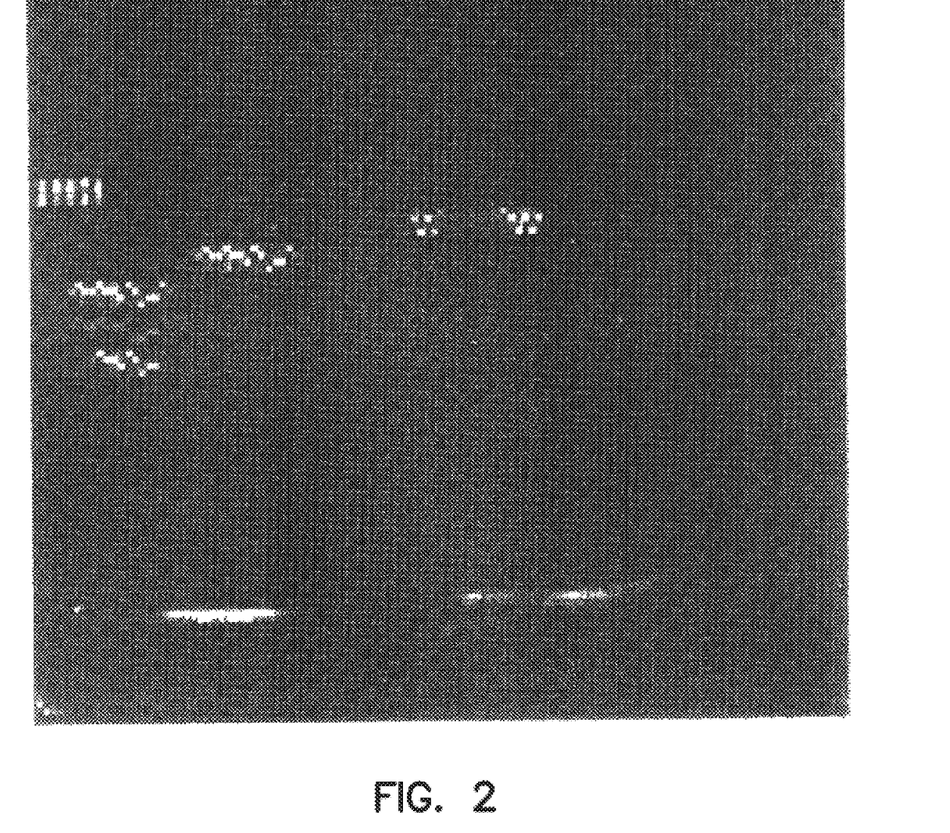
FIG. 2 is a scan of a substrate-bound oligonucleotide array hybridized four oligonucleotide targets (SEQ ID NOS: 1–4) with 5×SSPE and 5.2 M betaine.

Following hybridization, the two arrays were briefly rinsed in the same solutions they had been hybridized in. The arrays were mounted into flow cells filled with the same solutions. Scanning was done on a research grade confocal laser scanner at 100 μW power and 10 μ pixel resolution. Photographs of the two scans are attached as FIG. 1 and FIG. 2. FIG. 1 is a scan of the array hybridized with 5×SSPE and 1 mM CTAB. FIG. 2 is a scan of the array hybridized in the betaine solution.

It is evident from comparing the two scan files that in SX SSPE, these target nucleic acid molecules cross-hybridize broadly with this array. In addition, the four base differences between the oligos E6P-CYP2D6 (SEQ ID NO:3) and E6P-CYP2D7 (SEQ ID NO:4) (underlined in the sequences) and the three base deletion (lower case letters in the sequence) in oligo ΔL281 (SEQ ID NO:2) relative to the wild type tiling are not easily discriminated in 5×SSPE at room temperature. However, although the hybridization in betaine resulted in approximately a 4-fold lower signal, the base calling is sharply clear and can be read accurately.

Where single base discrimination is important in a hybridization array application, a hybridization optimizing agent, e.g., betaine, should be included in the hybridization optimization.

The present invention provides a novel method for performing assays on oligonucleotide arrays. While specific examples have been provided, the above description is illustrative and not restrictive. Many variations of the invention will become apparent to those of skill in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A method of detecting known polymorphic differences in a target nucleic acid molecule by performing a hybridization assay between the target nucleic acid molecule and a probe array wherein the probe array comprises a surface to which are covalently attached probes with different, known nucleotide sequences, at discrete, known locations;

the method comprises incubating the array with a hybridization mixture comprising the target nucleic acid molecule and betaine, determining the identity of the probes to which the target has hybridized and determining whether the target nucleic acid has a known polymorphic difference.

2. The method of claim 1, wherein the mixture comprises betaine in a concentration of about 1 M to about 10 M.

3. The method of claim 1, wherein the mixture comprises betaine in a concentration of about 4 M to about 6 M.

4. The method of claim 1, further comprising the step, after incubating the array, of washing the array with a solution that comprises betaine.

5. The method of claim 1, wherein the array has at least two probe locations.

6. The method of claim 1, wherein the array has a density of about five hundred to ten thousand probe locations per square cm.

7. The method of claim 1, wherein the array has a density of about ten thousand to one million probe locations per square cm.

8. The method of claim 1, wherein the array has a density of about one million to ten million or more probe locations per square cm.

9. The method of claim 1, wherein the target nucleic acid molecule is a cystic fibrosis nucleic acid or a human immunodeficiency virus nucleic acid.

10. The method of claim 1, wherein the target nucleic acid molecule is a cytochrome P-450 nucleic acid.

11. The method of claim 1, wherein the target nucleic acid molecule is a cytochrome P-450 CYP-2D6 nucleic acid.

12. A method for performing a hybridization assay between a target nucleic acid molecule and a probe array, wherein the probe array comprises a surface to which are covalently attached probes with different, known nucleotide sequences, at discrete, known locations;

the method comprises incubating the array with a hybridization mixture comprising the target nucleic acid molecule and betaine and determining the identity of probes to which the target has hybridized;

wherein the target nucleic acid molecule is a naturally-occurring nucleic acid molecule.

13. The method of claim 12, wherein the naturally-occurring nucleic acid molecule is a cystic fibrosis nucleic acid, or a human immunodeficiency virus nucleic acid.

14. The method of claim 12, wherein the target nucleic acid molecule is a cytochrome P-450 nucleic acid.

15. The method of claim 12, wherein the target nucleic acid molecule is a cytochrome P-450 CYP-2D6 nucleic acid.

16. The method of claim 12, wherein the mixture comprises betaine in a concentration of about 1 M to about 10 M.

17. The method of claim 12, wherein the mixture comprises betaine in a concentration of about 4 M to about 6 M.

18. The method of claim 12, further comprising the step, after incubating the array, of washing the array with a solution that comprises betaine.

19. The method of claim 12, wherein the array has at least two probe locations.

20. The method of claim 12, wherein the array has a density of about five hundred to ten thousand probe locations per square cm.

21. The method of claim 12, wherein the array has a density of about ten thousand to one million probe locations per square cm.

22. The method of claim 12, wherein the array has a density of about one million to ten million or more probe locations per square cm.

* * * * *